United States Patent [19]
Parrent, Jr. et al.

[11] Patent Number: 4,789,820

[45] Date of Patent: Dec. 6, 1988

[54] APPARATUS AND METHOD FOR SENSING MULTIPLE PARAMETERS OF SHEET MATERIAL

[75] Inventors: George B. Parrent, Jr., Chelmsford; Glenn W. Zeiders, Marblehead; James P. Reilly, Lexington; Antonio Khazen, Roslindale, all of Mass.

[73] Assignee: Hercules Incorporated, Wilmington, Del.

[21] Appl. No.: 884,642

[22] Filed: Jul. 11, 1986

Related U.S. Application Data

[63] Continuation-in-part of Ser. No. 817,273, Jan. 8, 1986, abandoned.

[51] Int. Cl.⁴ .......................................... G01R 27/04
[52] U.S. Cl. ....................... 324/58.5 R; 324/58.5 B; 324/58.5 A; 73/159; 73/73
[58] Field of Search ................... 73/73, 159; 324/58.5, 324/58, 71.3, 96

[56] References Cited

U.S. PATENT DOCUMENTS

| | | |
|---|---|---|
| 2,920,206 | 1/1960 | Williams et al. |
| 3,143,886 | 8/1964 | Lippke |
| 3,155,898 | 11/1964 | Chope .......................... 324/58.5 A |
| 3,460,030 | 8/1969 | Brunton et al. |
| 3,513,310 | 5/1970 | Chope et al. |
| 3,522,527 | 9/1967 | Williams et al. |
| 3,534,260 | 10/1970 | Walker |
| 3,586,601 | 12/1968 | Persik, Jr. et al. |
| 3,619,360 | 11/1971 | Persik, Jr. |
| 3,644,826 | 2/1972 | Cornetet, Jr. |
| 3,693,079 | 9/1972 | Walker |
| 3,737,770 | 6/1973 | Masson et al. |
| 3,789,296 | 1/1974 | Caruso, Jr. et al. |
| 3,815,019 | 6/1974 | Wiles |
| 3,851,244 | 11/1974 | Mounce |
| 3,889,121 | 6/1975 | Bossen |
| 3,913,012 | 10/1975 | Kujath |
| 4,155,035 | 5/1979 | Fitzky |
| 4,156,843 | 5/1979 | Strandberg, Jr. et al. |
| 4,193,027 | 3/1980 | Wyslouzil |
| 4,289,964 | 9/1981 | Baker |
| 4,297,874 | 11/1981 | Sasaki .......................... 324/58.5 C |
| 4,319,185 | 3/1982 | Hill |
| 4,368,421 | 1/1983 | Glander et al. |
| 4,399,403 | 8/1983 | Strandberg, Jr. et al. |
| 4,484,133 | 11/1984 | Riggin |
| 4,500,835 | 2/1985 | Heikkila |
| 4,674,325 | 6/1987 | Kiyobe .......................... 73/159 |
| 4,675,595 | 6/1987 | Hane .......................... 324/58.5 R |

OTHER PUBLICATIONS

"Optimize Press Section Operation with a Microwave Moisture Gauge", Hazelwood and Kenton, Paper Trade Journal, Oct. 2, 1972.

"Application of an On-Line Microwave Moisture Gauge at the Wet End", Richard A. Reese, Paper Trade Journal, Sep. 11, 1972.

Newspring Moisture and Basis Weight Measurement Using a Submilimeter Laser, by R. Boulay, B. Drouin, R. Gagnon and J. R. Izatt, Journal of Pulp and Paper Science, 7/1984.

*Primary Examiner*—Reinhard J. Eisenzopf
*Assistant Examiner*—Jose M. Solis
*Attorney, Agent, or Firm*—Finnegan, Henderson, Farabow, Garrett & Dunner

[57] ABSTRACT

A method and apparatus for simultaneously generating spatial profiles of moisture, thickness, and basis weight across a moving web of paper in a paper making machine. The apparatus includes a plurality of means for generating first and second beams of coherent microwave radiation and for generating signals proportional to the intensity of radiation applied to, reflected from, and transmitted through the web. The incident, reflectance, and transmittance signals for the two frequencies are used to solve simultaneous equations to generate moisture, thickness, and basis weight values at various positions across the web.

50 Claims, 7 Drawing Sheets

APPARATUS AND METHOD FOR SENSING MULTIPLE PARAMETERS OF SHEET MATERIAL

This application is a continuation-in-part of U.S. patent application Ser. No. 817,273, now abandoned, entitled Apparatus and Method For Sensing Multiple Parameters of Sheet Material, filed Jan. 8, 1986 by George B. Parrent Jr., Glenn W. Zeiders, and James P. Reilly and assigned to the assignee of the present invention.

BACKGROUND OF THE INVENTION

The invention relates generally to methods and apparatus for sensing parameters of sheet material and, more particularly, to sensing multiple parameters of sheet material manufactured in a continuous moving web.

In materials manufacturing, it is often desired to monitor one or more parameters of the product being manufactured. It is particularly important in paper manufacturing to maintain a constant awareness of thickness and moisture content of the web on the paper making machine. It is also desirable to provide a continuous measurement of basis weight of the paper; that is, the weight per unit area.

Many methods are known in the prior art for providing such information. For example, it is known that moisture content in a moving paper web can be measured by microwave techniques as shown, for example, in U.S. Pat. No. 4,484,133. As disclosed therein, a signal related to moisture content and derived from microwave energy can be corrected for thickness of the paper.

It is also known in the prior art to provide various methods for monitoring the thickness of the web. These techniques include the use of microwaves to measure thickness of a moving sheet as disclosed, for example, in U.S. Pat. No. 3,737,770. However, none of the methods known in the prior art, including the aforementioned United States patents, provide satisfactory means for simultaneously generating a spatial profile of moisture and thickness across the width of the web. It would therefore be desireable to provide such simultaneous spatial profile.

It is also known in the prior art to provide a measurement of basis weight. However, such prior art basis weight measurement techniques do not provide satisfactory means for generating an indication of absolute basis weight across the width of the web simultaneously with the production of a similar range of measurements for thickness and moisture. Furthermore, prior art techniques for generating measurements of parameters across the face of the web often involve complex moving-part scanning arrangements. Accordingly, it is desirable to provide apparatus and methods for simultaneously generating spatial profiles of moisture, thickness, and basis weight which eliminate the need for movable components of sensing apparatus.

SUMMARY OF THE INVENTION

In accordance with the principles of the present invention, there is provided apparatus for sensing the characteristics of sheet material, comprising radiating means for generating a plurality of beams of coherent electromagnetic radiation, each of the beams having a different frequency, and for directing the beams against the material at a suitable angle of incidence. The apparatus also includes first signal generating means for generating separate reflectance and transmittance signals for each of the beams proportional to the intensity of each of the beams reflected from and transmitted through the material, respectively. Finally, the apparatus includes processing means for producing moisture and thickness signals calculated from the plurality of reflectance and transmittance signals. In a preferred embodiment, the radiating means includes a plurality of microwave oscillators, each generating a microwave signal of a different frequency. The apparatus includes a plurality of such radiating means spatially distributed across the width of a moving web of sheet material. In the preferred embodiment, the processing means produces ratios of reflectance to transmittance signals for each frequency and solves a set of simultaneous equations analyzing the constructive and/or destructive interference effects of the coherent microwave radiation relating to the water content and thickness ratio of the sheet.

In a first alternative embodiment, the apparatus includes second generating means for generating a reference signal proportional to basis weight at a reference position, the processing means then generating a spatial profile of dry basis weight of the material calculated from the reference signal and the moisture and thickness signals.

In a second and preferred alternative embodiment, the apparatus includes incident signal generating means for generating separate incident signals for each of the beams, the incident signals being proportional to the intensity of each of the beams incident upon the material. The apparatus further includes processing means for producing moisture, thickness, and basis weight signals calculated from the plurality of incident, transmittance, and reflectance signals. In the second alternative preferred embodiment, the radiating means includes a plurality of microwave oscillators, each generating a microwave signal of a different frequency. The apparatus includes a plurality of such radiating means spatially distributed across the width of a moving web of sheet material and the processing means produces ratios of incident to transmittance signals for each frequency and solves a set of simultaneous equations analyzing the constructive and/or destructive interference effects of the coherent microwave radiation relating to the water content, thickness, and basis weight of the sheet.

DESCRIPTION OF THE PREFERRED EMBODIMENT

The present invention employs the principles of constructive and destructive interference produced by reflection and refraction of coherent radiation. A brief discussion of these principles will therefore be helpful in describing the preferred embodiment of the invention.

When a beam of coherent radiation such as microwave radiation is directed at a dielectric material of finite thickness, several phenomena occur. A portion of the incident radiation is reflected from the first surface and the non-reflected portion passes through the surface and is partially absorbed by the inner material. The internal portion impacts the second surface of the dielectric, and is reflected back through the material. This process of transmission, reflection, and absorption is repeated ad infinitum until the microwave energy is reduced to zero. These processes occur regardless of the state of the incident radiation. That is, whether the microwaves are collimated or focusable or diffuse the same phenomena occur. However, the manner in which the repetitively reflected or transmitted components interact with each other is strongly dependent on the state of coherence of the incident radiation.

If the beam is not diffuse, the reflected or transmitted components are said to "add coherently". Both constructive and destructive interference can take place; that is, the components may be combined either in phase or out of phase. In any case, the components combine in a fixed phase relationship determined solely by the wavelength of the microwaves, the thickness, index of refraction, and the geometry of the dielectric.

If the incident radiation is diffuse, reflection and transmissions take place over a wide range of angles. Its behavior depends in a complex way not only on the geometry of the dielectric material but also on the detailed description of the beam shape. If a microwave beam is used to measure moisture content of, for example, paper, it is necessary to carefully analyze the geometric configuration of the measurement. Each transmitted component has passed through more thicknesses of the moisture-laden material than its predecessor and for each component the material appears thicker than for the preceding component. These phenomena are well known and have influenced the design of many of the prior art systems using microwave measurement of moisture content.

Figure 1:
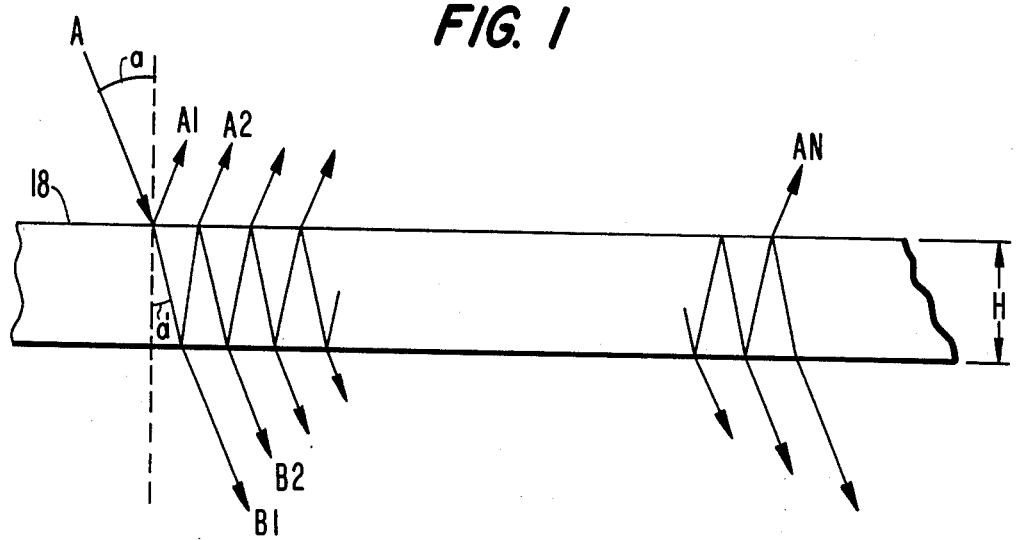
FIG. 1 is a diagram illustrating the transmission and reflection behavior of a beam of coherent radiation incident upon sheet material.

Referring now to the drawings, FIG. 1 shows a dielectric sheet of paper 18 of thickness H, with parallel sides. Throughout the drawings, identical elements are referred to by identical reference characters. A coherent beam of microwave radiation is incident at an angle, a, relative to the normal and is shown in FIG. 1 as a single ray, A. The portion of this beam reflected from the front surface is denoted by a ray A1. The portion transmitted through the paper and out the other side is denoted by a ray B1. Note that ray B1 has passed through the paper once but that its path length through the paper is not equal to H, but rather to H divided by the cosine of a' where a' is the angle that ray B1 makes with the normal while traveling through the interior of paper 18. Angle a' is determined by Snell's Law. The portion of beam A reflected from the lower surface and transmitted through the upper surface is denoted by A2. Note that ray A2 has passed through paper 18 twice, thus suffering an attenuation equivalent to passage through a paper twice the thickness of paper 18. The portion of beam A reflected from the upper surface and transferred through the lower surface is denoted by B2 and, as can be seen in FIG. 1, has now made three passes thorough the paper. This process is continued until the transmitted and reflected components of beam A have been reduced to zero.

From FIG. 1 it is clear that if all of the reflected energy is collected with one collector and all of the transmitted energy with another collector, both the transmitted and reflected energy would be complex functions of the thickness H of paper 18 and the absorption coefficient of paper 18. The absorption is a function of the moisture content in the paper and the dielectric constant of the dry paper.

In order to construct a microwave system for measuring the moisture content of the paper, it is necessary to consider the thickness. In the prior art, there was an awareness that there are several components to energy measurements including the reflected, transmitted, and absorbed components, and effects of multiple reflection phenomena. Prior art methods were characterized by attempts to either minimize the effects of such phenomena or compensate for them. However, if the thickness of the paper varies, either randomly as part of the process or from type to type by deliberate choice, then prior art techniques involving compensation and assumptions of simplification were not effective.

In the present invention no attempts are made to compensate for the coherent effects in order to eliminate the dependence on thickness. Instead, such effects are exploited in order to simultaneously determine thickness and moisture without making any assumptions about either. These simultaneous measurements are accomplished by simultaneously illuminating the material to be measured with two radiation beams having different wavelengths, thus yielding two equations in two unknowns for each point at which the transmission and reflectance is measured. These two simultaneous equations are then solved to yield thickness and moisture. Measurements at a third wavelength can be performed in certain applications as a validity check.

The measurements of reflected and transmitted energy through the material to be analyzed can be formed into a ratio R/T of reflected power to transmitted power.

The ratio R/T of reflected power to transmitted power reduces to the product of two functions of the complex index of refraction of the moist paper $n+ik$: a "surface" factor $S^2$ and a "bulk" factor $Sin^2$ where:

$$S^2 = \frac{(n^2 + k^2 - 1)^2 + 4n^2k^2}{4(n^2 + k^2)} \quad (1)$$

$$\sin^2 = \tfrac{1}{2}\left[\cosh\left(4\frac{\pi kH}{\lambda}\right) - \cos\left(4\pi\frac{nH}{\lambda}\right)\right] \quad (2)$$

H = paper thickness;
λ = wavelength; and
H and λ have the same units.

We have determined that for moisture ranges of 0.1–1–60% and thickness ranges of 0.001–0.25 that the power ratio R/T can be approximated by:

$$\frac{R}{T} = \left[ e^{-\frac{4\pi kH}{\lambda}} \right] \left[ \frac{(n^2 - k^2 - 1)^2 + 4n^2k^2}{8(n^2 + k^2)} \right] \left[ 0.5\, e^{\frac{4\pi kH}{\lambda}} + 0.5\, e^{-4kH} - \cos\left(\frac{4\pi nH}{\lambda}\right) \right]$$

Paper thickness H and moisture content M are thus given by parametric solution of the above equation for the two variables of H and M, where M determines n and k according to:

$$n = n_p(1-M) + n_w \cdot M$$

$$k = k_p(1-M) + k_w \cdot M$$

where $n_p$ and $k_p$ are the real and imaginary indices of refraction, respectively, of the dry paper being measured.

The values of $n_w$ and $k_w$ are the real and imaginary indices of refraction by water and have been determined experimentally. They can be approximated by the following expressions over the frequency range of 30–100 GHz (0.3 cm–1.0 cm):

$$n_w = 3.33\lambda + 2.667$$

$$k_w = 4.08\lambda - 2.04\lambda^2 + 0.96$$

for $0.3 < \lambda < 1.0$ cm.

Figure 2:
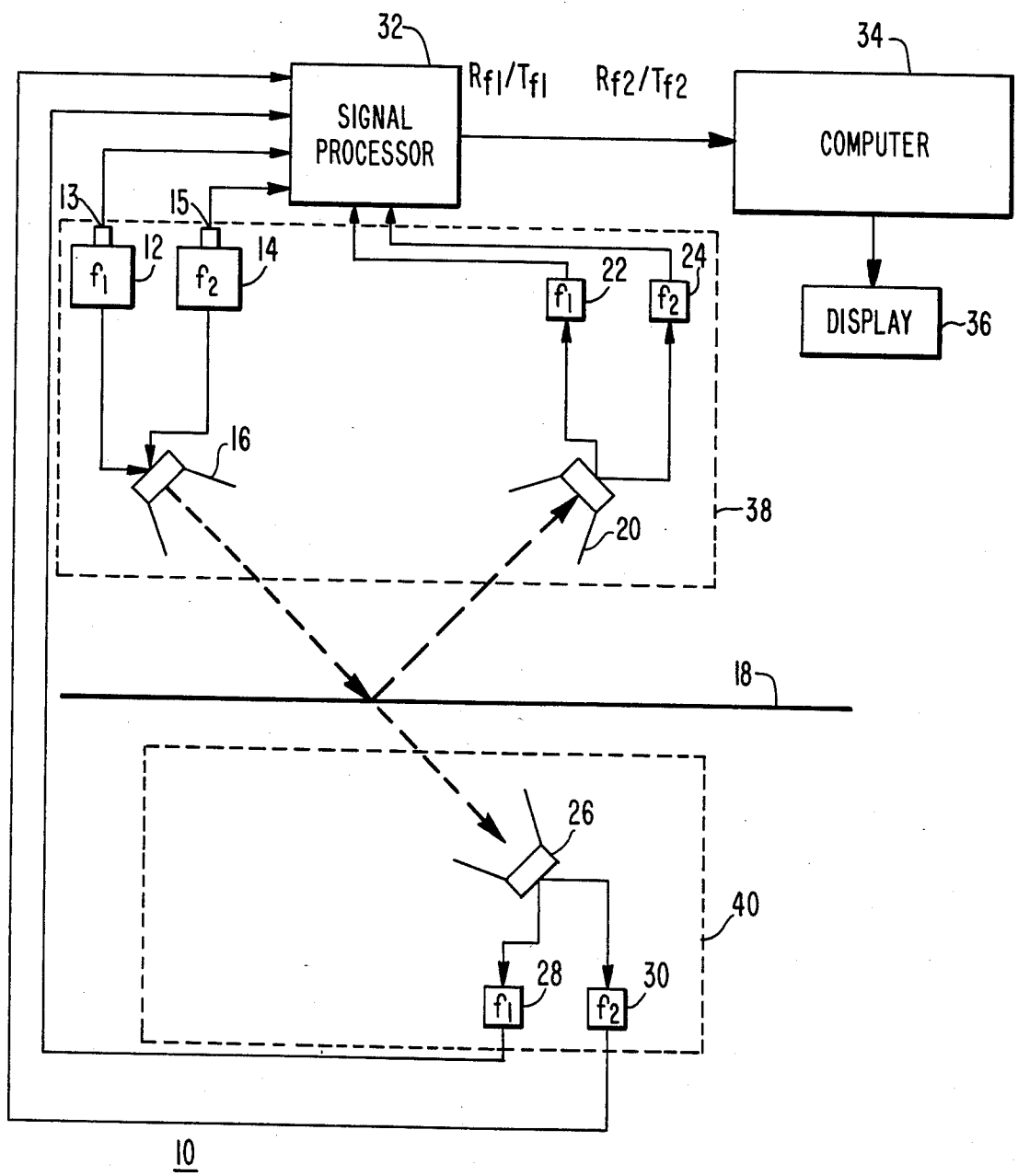
FIG. 2 is a schematic diagram of a preferred embodiment of the invention.

Referring now to FIG. 2, there is shown a block diagram of a system 10 embodying the invention. A pair of oscillators 12 and 14 generate electromagnetic radiation having frequencies of $f_1$ and $f_2$, respectively. The wavelength of the highest frequency should be at least four times the thickness of material being analyzed, to avoid ambiguities in results. In the preferred embodiment, oscillators 12 and 14 generate microwave radiation at frequencies of 94 Ghz and 47 Ghz, respectively. Signals from oscillators 12 and 14 are supplied to a transmitting antenna 16 which produces a pair of beams of coherent microwave radiation which are directed against a sheet of paper 18 at an area of incidence. The invention thus includes radiating means for generating a plurality of beams of coherent electromagnetic radiation, each of the beams having a different frequency, and for directing the beams against sheet material at an area of incidence. As embodied herein, the radiating means comprises oscillators 12 and 14, and antenna 16.

As can be seen in FIG. 2, a portion of the beams directed by antenna 16 are reflected by paper 18 to a reflectance receiving antenna 20. The first and second beams having frequencies of $f_1$ and $f_2$ are directed to first and second reflectance detectors 22 and 24. Detectors 22 and 24 produce reflectance signals as output, the reflectance signals being proportional to the intensity of each of the beams of the respective frequencies reflected from paper 18.

A transmittance receiving antenna 26 is positioned below paper 18 and collects that portion of the first and second beams from antenna 16 which are transmitted through paper 18. Antenna 26 directs the transmitted beams having frequencies of $f_1$ and $f_2$ to first and second transmittance detectors 28 and 30, respectively. Detectors 28 and 30 produce transmittance signals which are proportional to the intensity of each of the beams transmitted through paper 18.

The invention, therefore, includes first signal generating means for generating separate reflectance and transmittance signals for each of the beams, the signals being proportional to the intensity of each of the beams reflected from and transmitted through the material being analyzed, respectively. As embodied herein, the first signal generating means comprises transmittance receiving antenna 26, first and second transmittance detectors 28 and 30, antenna 20, and first and second reflectance detectors 22 and 24.

The reflectance and transmittance signals from detectors 22, 24, 28, and 30 are supplied to a signal processor 32 which produces ratio signals $R_{f1}/T_{f1}$ and $R_{f2}/T_{f2}$. The ratio signals are signals having a value proportional to the ratio of the intensities of microwave radiation reflected from and transmitted through paper 18 for both the first and second frequencies. The ratio signals are then supplied to a computer 34 where moisture and thickness signals are generated from the ratio signals by solutions of equation (4). Computer 34 then produces signals representative of both moisture content and thickness and supplies such signals to a display device 36.

Various configurations are possible for signal processor 32, computer 34, and display device 36. For example, signal processor 32 may comprise a plurality of analog-to-digital converters for converting the reflectance and transmittance signals from detectors 22, 24, 28 and 30 into digital signals and a microprocessor for computing digital ratio signals R/T. Computer 34 may be a computer of moderate processing power such as an IBM PC personal computer. Display device 36 may comprise a CRT display in which moisture content and thickness values are displayed in alphanumeric characters. Alternatively, display device 36 may comprise a plurality of large numeric digital read out devices. The functions of signal processor 32 and computer 34 may alternatively be performed by a plurality of analog-to-digital converters supplying output signals directly to a computer for computation of ratio signals and solution of equation (4) discussed previously.

Oscillators 12 and 14, transmitting antenna 16, reflectance receiving antenna 20, and detectors 22 and 24 together form a reflectance unit 38 for producing reflectance signals. Transmittance receiving antenna 26 and detectors 28 and 30 together form a transmittance unit 40 for producing transmittance signals.

Figure 3:
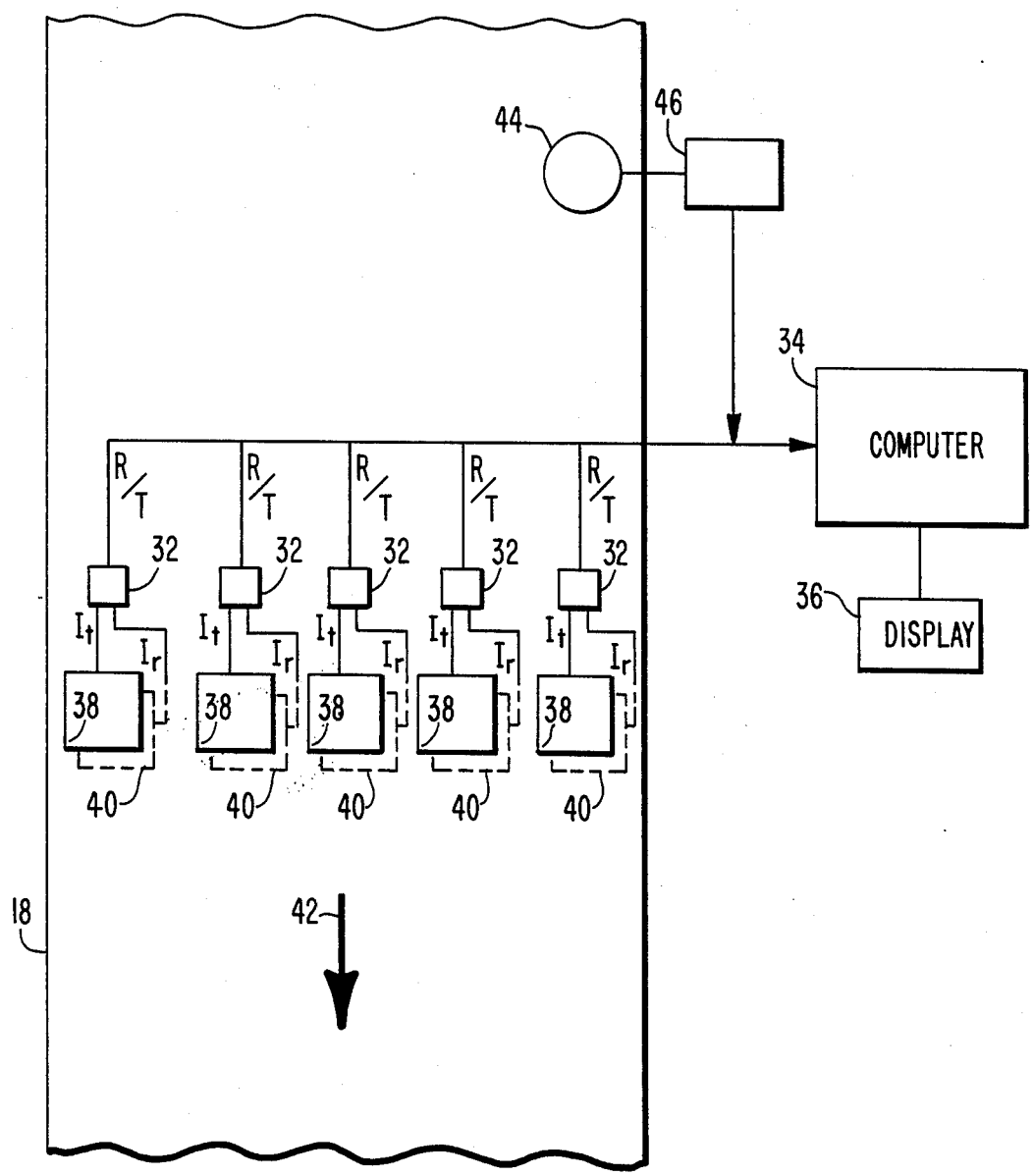
FIG. 3 is a schematic diagram of a further preferred embodiment of the invention.

Referring now to FIG. 3, there is shown a block diagram of a further preferred embodiment of the invention. As can be seen in FIG. 3, a plurality of reflectance units 38 and transmittance units 40 are disposed on opposite sides of a moving web of paper 18 being manufactured on a Fourdrinier paper making machine and moving in a direction indicated by arrow 42. The transmittance and reflectance signals of both frequencies, indicated in FIG. 3 by $I_t$ and $I_r$, respectively, are supplied to signal processors 32. As shown in FIG. 3, several units 38 or 40 may be connected to a single signal processor 32. Signal processors 32 produce digital signals representative of the intensities of microwave radiation reflected from and transmitted through paper web 18 for each frequency at various positions across the web. The intensity signals are then supplied to computer 34 where ratio signals R/T are calculated. Alternatively, it may be desirable in some applications to connect signal processors 32 to the outputs of both a reflectance unit 38 and a transmittance unit 40 and to compute R/T signals in signal processors 32.

Also shown in FIG. 3 is a basis weight monitor 44 which generates a signal proportional to basis weight of the moving web 18 at a fixed position with respect to the edge of the web 18. The output of basis weight monitor 44 is supplied to a second signal processor 46 which converts an analog signal produced by monitor 44 into a digital signal and provides appropriate scaling functions before transmitting a digital signal to computer 34. Basis weight monitor 44, in a preferred embodiment, is a Type 1000 monitor commercially available from the Ohmart corporation. The Type 1000 monitor produces a stream of beta radiation from a radioactive cesium source and measures the amount of beta radiation transmitted through the moving web 18 using a radiation detector which produces an analog output signal proportional to the electron flux received. Other types of basis weight monitors may be employed, including, for example, an electron gun and detector combination.

The signal from monitor 44 as processed by signal processor 46 is converted by computer 34 into a signal representative of ambient basis weight of the moist paper at a reference position spaced from the edge of web 18, as shown by the position of monitor 44 with respect to the right hand edge of web 18.

Reflectance and transmittance units 38 and 40 produce intensity signals $I_r$ and $I_t$ which are used by computer 34 to produce ratio signals R/T at a plurality of positions across the web 18 perpendicular to the direction of arrow 42. These ratio signals for frequencies $f_1$ and $f_2$ are used to compute moisture content and thickness values for the respective positions across the web in the manner previously described. The value of moisture content of the web at the position of basis weight monitor 44 is combined with the moist basis weight value obtained from monitor 44, thus deriving dry basis weight for the monitor position according to the following formula:

Dry basis weight(monitor) = ambient moist basis weight(monitor) × (1-moisture)

The thickness values across the web may be used with the dry basis weight value at the monitor position to yield a spatial profile of dry basis weight across the web.

Figure 4:
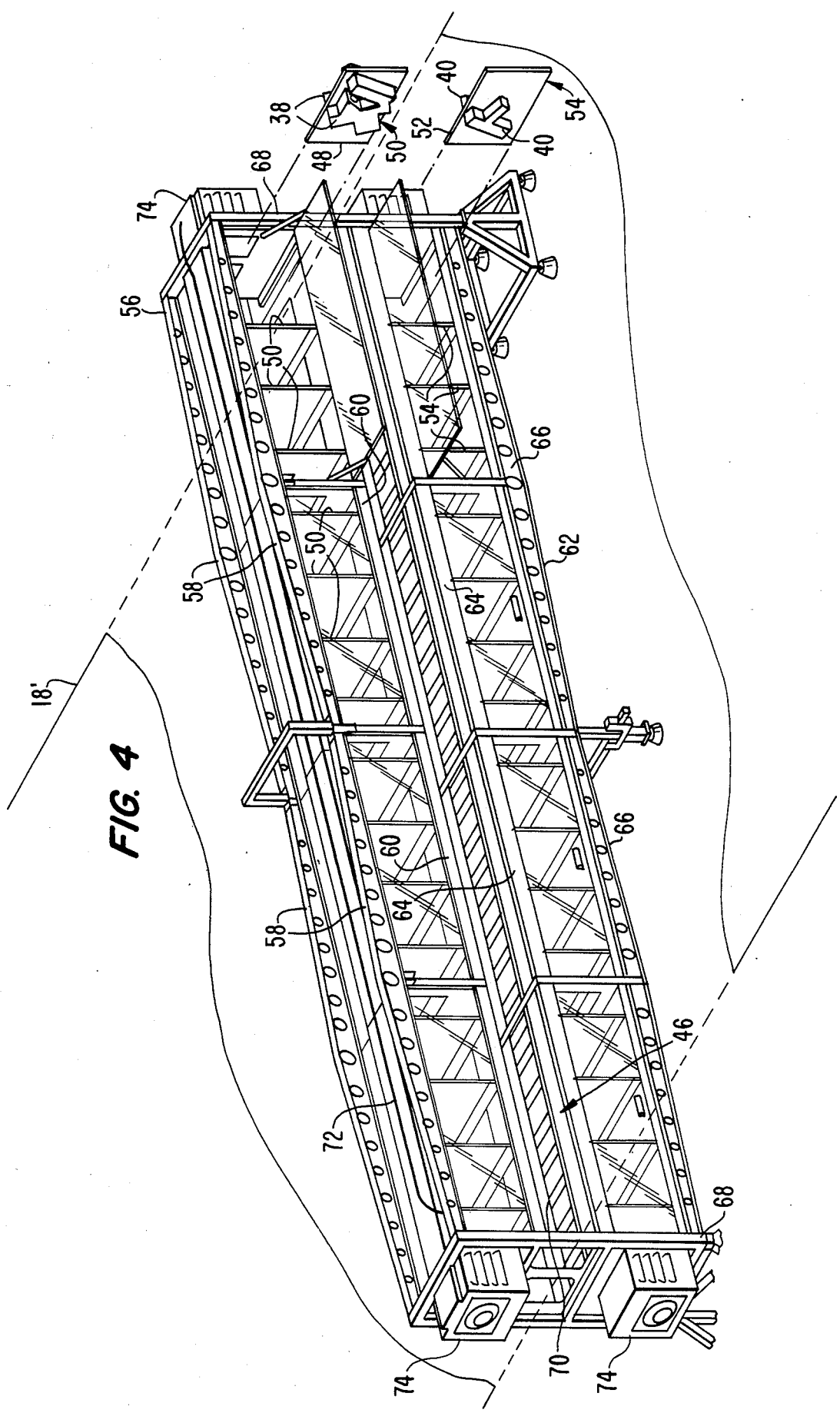
FIG. 4 is a perspective view of a sensing array which is a further preferred embodiment of the invention.

Referring now to FIG. 4, there is shown a perspective view of a 32-position sensing array 46 which produces moisture, thickness, and basis weight profiles across the width of the paper web output 18' of 300 inch Fourdrinier paper making machine. There are gaps in coverage between the positions of the array, but the majority of the paper across the width of the web is monitored by the 32 position array 46, and for many applications such gaps are not significant. In certain applications it may be desirable to provide narrower gaps in coverage and thus more positions could be supplied in array 46. If enough positions are supplied, coverage can be essentially continuous across the width of the web.

As can be seen at the far right of FIG. 4, a pair of reflectance units 38 are mounted on opposite sides of a reflectance mounting board 48 to form a reflectance module 50. A pair of transmittance units 40 are mounted on opposite sides of a transmittance mounting board 52 to form a transmittance module 54. Array 46 contains 16 reflectance modules 50 each mounted in a reflectance frame 56 formed of a plurality of horizontal upper reflectance support beams 58 and lower reflectance support beams 60. Reflectance frame 56 supports each of the reflectance modules 50 juxtaposed, that is, positioned side by side, in a horizontal plane.

Array 46 also includes a transmittance frame 62 formed by a plurality of horizontal upper transmittance support beams 64 and lower transmittance support beams 66. Transmittance frame 62 supports transmittance modules 52 juxtaposed parallel to the horizontal plane of the reflectance modules 50.

Array 46 further comprises vertical support members 68 which support transmittance frame 62 and reflectance frame 56 in a manner so as to define an elongated opening therebetween through which passes moving web 18' of paper to be analyzed. Vertical supports 68 thus support each of the reflectance modules 50 in vertical alignment with a corresponding one of the transmittance modules 54 such that an aligned pair of reflectance unit 38 and transmittance unit 40 are associated with a predetermined area of incidence equally spaced across moving web 18'. The invention thus comprises means for supporting the reflectance and transmittance frames in a manner so as to define an elongated opening therebetween parallel to the horizontal plane of the reflectance and transmittance modules and adapted to receive a moving web of material to be analyzed, the supporting means supporting each of the reflectance modules in vertical alignment with a corresponding one of the transmittance modules. As embodied herein, the supporting means comprises vertical supports 68.

Cable trays are formed between upper reflectance support beams 58 and below transmittance frame 62 and contain a plurality of cables 72 connected to each of the reflectance and transmittance units 40. Cables 72 are connected to power supply modules 74 which supply operating power to reflectance and transmittance units 38 and 40. Cables 72 are also connected to computer 34 positioned at a convenient location remote from array 46. Computer 34 and display device 36 are accordingly not shown in FIG. 4. Cables 72 are connected through signal processors 32 on each of the reflectance and transmittance modules 50 and 54 to each the transmittance and reflectance detectors 22, 24, 28, and 30. The invention thus comprises means for connecting each of the transmittance and reflectance detectors to the processing means. As embodied herein, such connecting means comprises signal processors 32 and cables 72.

In alternative embodiments, more or fewer than two reflectance units 38 or transmittance units 40 may form each reflectance module 50 or transmittance module 54. The design considerations involve the cost and processing power of signal processor 32, and include trade-offs well-known to those skilled in the art.

Figure 5:
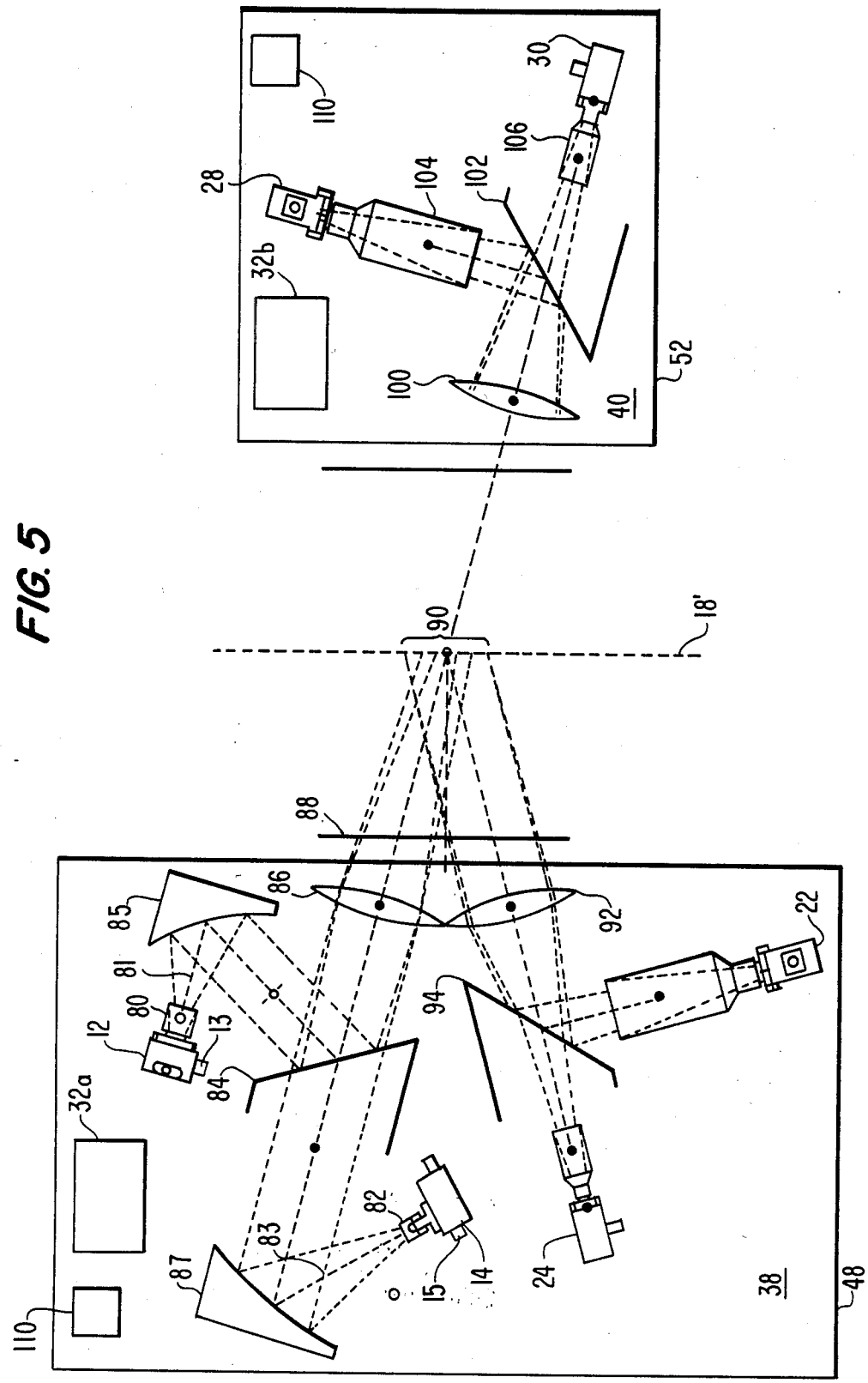
FIG. 5 is a plan view of reflectance and transmittance modules of the array of FIG. 4.

The construction of reflectance unit 38 and transmittance unit 40 is shown more clearly in FIG. 5. Oscillator 12 comprises a Gunn diode oscillator generating a microwave carrier frequency of 47 Ghz. An FM modulator is mounted within the housing of oscillator 12, and is not visible in FIG. 5. The modulator associated with oscillator 12 provides FM modulation at a frequency of 20 Khz. The output of oscillator 12 is coupled to a conical horn antenna 80 to form a beam 81.

Oscillator 14 comprises a Gunn diode oscillator producing a microwave carrier frequency of 94 Ghz. A modulator not visible in FIG. 5 is mounted within the housing of oscillator 14 and provides FM modulation of the carrier frequency of oscillator 14 at a frequency of 21 Khz. The output of oscillator 14 is coupled to a conical horn antenna 82 to form a beam 83 polarized orthogonally to beam 81. Oscillators 12 and 14 may be type GDM Gunn diode microwave sources commercially available from Millitech of South Deerfield, Mass.

Beams 81 and 83 are reflected by mirrors 85 and 87 toward a dielectric supported grid filter 84 functioning as a beam combiner. Mirrors 85 and 87 may be off-axis parabolical mirrors such as type GMP available from Millitech. The polarization of oscillators 12 and 14 and the orientation of grid filter 84 are such that beam 81 is reflected from one surface of filter 84 and beam 83 passes essentially unimpeded through filter 84 such that beams 81 and 83 are combined into a common path. The combined beams are then passed through a millimeter microwave plano-hyperbolic lens 86 of dielectric material such as material identified by the trademarks REX-OLITE, TEFLON, or TPX. Combined beams 81, 83 pass through lens 86 and a window 88 and are focused upon an area of incidence 90 on web 18'.

The invention thus includes first focusing means downstream from filter 84 (functioning as a beam combiner) for collimating first and second beams 81 and 83 and for focusing first and second beams 81 and 83 against the material 18' to be analyzed. As embodied herein, the first focusing means comprises lens 86.

Reflectance unit 38 also includes a second lens 92 receiving the portion of beams 81 and 83 reflected from web 18'. Beams 81 and 83 passing through lens 92 are focused upon a reflectance beam splitter 94 which also comprises a dielectric supported grid filter. Grid filters 84 and 94 may be, for example, type GDS filters available from Millitech. Reflectance unit 38 also includes first and second reflectance detectors 22 and 24. Detectors 22 and 24 comprise polarization sensitive microwave detectors which, in the preferred embodiment, employ Schottky barrier beam lead diodes for receiving frequencies of 47 GHz and 94 GHz, respectively. Detectors 22 and 24 may be type DXP planar detectors commercially available from Millitech.

The orientation of detectors 22 and 24, and of reflectance beam splitter 94 is such that first beam 81 is reflected from reflectance beam splitter 94 into detector 22. Beam 83 passes essentially unimpeded through reflectance beam splitter 94 into detector 24.

The invention thus includes second focusing means for receiving the first and second beams reflected from the material to be analyed. As embodied herein, the second focusing means comprises lens 92.

Transmittance unit 40 includes a lens 100 oriented to receive that portion of beams 81 and 83 which are transmitted through web 18'. Lens 100 is similar in type to lenses 86 and 92, all of which may be type MML lenses available from Millitech. The transmitted portion of beams 81 and 83 passes through lens 100 to a transmittance beam splitter 102 which in the preferred embodiment comprises a dielectric supported grid such as type GDS available from Millitech. Transmittance unit 40 also includes transmittance detectors 28 and 30 identical to reflectance detectors 22 and 24, respectively, and oriented in relation to transmittance beam splitter 102 such that the transmitted portion of beam 81 is reflected from beam splitter 102 through antenna 104 to detector 28 and the transmitted portion of beam 83 passes essentially unimpeded through beam splitter 102 through antenna 106 to detector 30.

Figure 6:
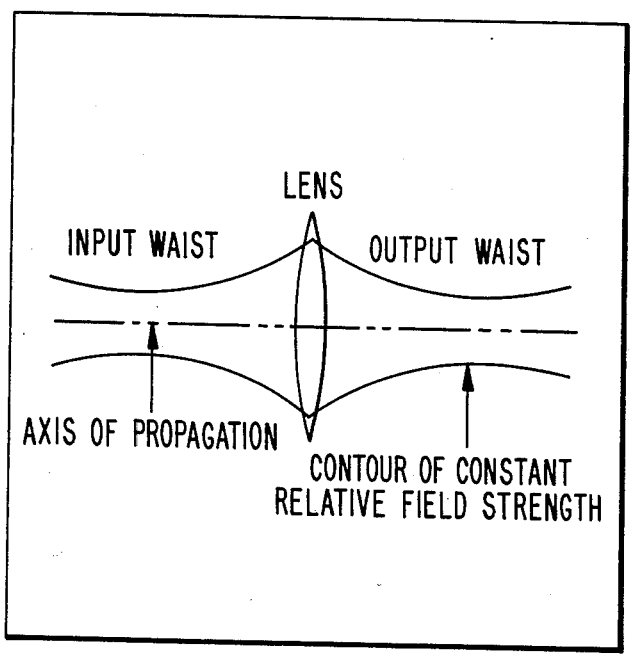
FIG. 6 is a schematic diagram illustrating the operation of a microwave lens of the modules of FIG. 5.

Reflectance unit 38 and transmittance unit 40 constitute a Gaussian microwave optics system in which beams 81 and 83 have a Gaussian distribution of the electric field perpendicular to the axis of propogation. Such a Gaussian beam preserves its form as it propogates away from regions where its diameter is a minimum; that is, the beam waist. Beam waists may be reimaged by lens such as lenses 86 and 92, as shown in FIG. 6. The characteristics of the input and output waists as shown in FIG. 6 are determined by the specific physical configuration and axes of curvature of such lenses. In the preferred embodiment, lens 86 focuses combined beams 81 and 83 to form an output waist at the area of incidence 90 of web 18'. Lens 92 is formed such that the input waist of lens 92 is larger than the output waist of lens 86. In this manner, the value of reflectance and transmittance signals obtained by units 38 and 40 is less sensitive to tilt of the plane of web 18'. In the preferred embodiment, the output waists of lens 86 are 0.6 and 1.5 cm and the input waists of lens 92 are 2.5 cm.

It is not absolutely necessary that beams 81 and 83 be modulated and orthogonally polarized. However, by providing such modulated beams with different modulation frequencies and polarization, more precise values of ratio signals R/T can be obtained. Moreover, by choice of different modulation frequencies for oscillators 12 in adjacent reflectance units and for oscillators 14 therein, greater isolation between reflectance modules can be obtained, thereby permitting a greater total number of such modules for a given width of web 18' to provide a more detailed analysis of the parameters across the web.

In order to provide the benefits of the invention at the lowest cost, however, all transmittance and reflectance modules are identical. The modulators of each such module have a variable modulation frequency. Each module includes, as a part of signal processor 32, separate microprocessors 32a and 32b mounted on the mounting board of each reflectance and transmittance module, respectively. Each module is mounted in its associated frame in a slide in, plug in manner. Each slot of the transmittance and reflectance frames is specified during manufacture of the array to be associated with a specific modulation frequency, chosen for maximum isolation of adjacent modules. The slot includes coded connection means such as an 8-pin female connector, each pin of the connector being connected to a logic high or logic low voltage source. Each transmittance and reflectance module includes an 8-pin male connector 110 compatible with the female connector of each slot. When the module is firmly and completely mounted in its associated slot, the male connector of each module is thus connected to a pattern of logic high and logic low signals. Microprocessors 32a and 32b on board each module are connected to the associated 8-pin male connector 110 and interpret the logic pattern thereon to set modulation frequencies of modulators associated with modulators 12 and 14 of each reflectance module. In this manner, optimum modulation frequency operation for maximum performance and isolation is obtained while retaining the benefits of identical hardware in each module.

Various modifications are of course possible in the present invention. For example, the embodiment shown in FIG. 4 provides reflectance modules mounted above the moving web and transmittance modules mounted below. In certain installations, the opposite configuration can easily be provided. Furthermore, it is not necessary that the transmittance and reflectance frames be physically connected as shown in FIG. 4. It may be desirable in certain applications to provide the reflectance frame below the moving web and the transmittance frame mounted a significant distance above the moving web. With proper design, the transmittance modules may be mounted upon the ceiling, so long as appropriate alignment is maintained between cooperating transmittance and reflectance modules.

In certain environments, it may be desirable to provide a ratio signal measured at a third frequency. Specifically, it may be desired to make such third frequency measurement at the same position relative the edge of the web as that of basis weight monitor 44. Simultaneous measurements are made to simultaneously provide a ratio signal R/T at first and second frequencies $f_1$ and $f_2$ spaced across the web, to provide a ratio signal R/T at a third frequency, and to provide a measurement of electron absorption at the third frequency position to provide a measurement of moisture dependent basis weight at that positon.

The second step is to solve equation (4) previously set forth for the real and imaginary components of the index of refraction of the moist paper and to use the results of these solutions along with the ratio signals R/T of frequencies $f_1$ and $f_2$ across the web to provide signals representative of moisture content and thickness. Finally, these results are used to compute density and basis weights to derive both ambient basis weight and bone-dry basis weight values to provide spatial profiles thereof across the web.

Figure 7:
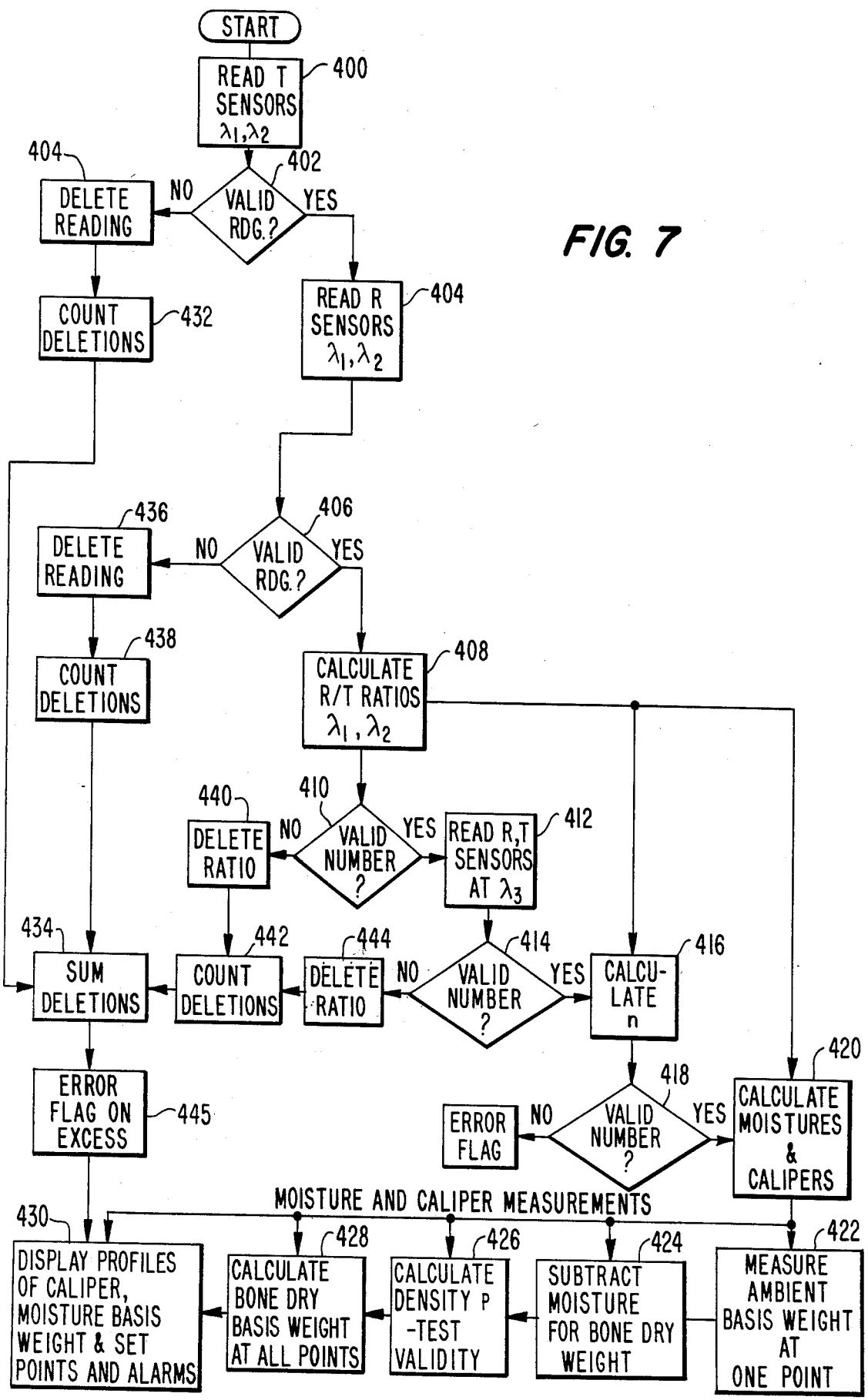
FIG. 7 is a flow chart of the calculations performed by the computer shown in FIGS. 2 and 3.

In FIG. 7, there is shown a flow chart of the processing provided by computer 34. At block 400, transmission signal intensity values $I_t$ are read from all transmittance units 40. A determination is made at block 402 if the readings are valid. If so, reflectance intensity signals $I_r$ produced by reflectance units 38 are read for each wavelength at each position. A determination is made at block 406 if the reflectance readings are valid.

Valid readings are then used at block 408 to calculate R/T ratios for two wavelengths at all positions. Again, validity checks are performed at block 410. If all ratios are valid, reflectance and transmittance intensity values at the third wavelength measured at the position of basis weight monitor 44 are read. Validity checks are performed on these values and, if valid, values for the index of refraction n of each position are calculated at block 416 from R/T ratios at all three wavelengths. If these values are valid as determined at block 418, moisture and caliper for each position are calculated by solution of equation 4 at block 420.

At block 422, an ambient basis weight measurement is made by monitor 44. Bone dry basis weight at the position of monitor 44 is then calculated at block 424 from moisture and ambient basis weight values at the position of monitor 44. At block 426, density is calculated from thickness and dry basis weight. Bone dry basis weight at all points is then calculated at block 428 from moisture, thickness, and density values. This information is then displayed at block 430.

If an invalid reading is detected at block 402, the reading is deleted at block 404. Such deletions are counted and accumulated at block 432 and summed at block 434. Similar deletion counts are obtained from blocks 406, 436, 438; blocks 410, 440, and 442; and blocks 414, 444, and 442. All deletions are summed at block 434. If the total number of deletions exceeds a predetermined limit value, an error indication is generated at block 445. This information is then provided to block 430 for display.

In a second alternative embodiment, signals indicative of basis weight are calculated directly from radiation signals in the same manner as moisture and caliper. Specifically, such basis weight signals are calculated from ratios of transmittance to incident radiation and reflectance to incident radiation with respect to web 18.

In a form analogous to equation (4), ratios of reflectance to incident and transmittance to incident radiation can be set forth in more rigorous form as:

$$\frac{R_2}{I_2} = \frac{\left[\frac{2(1-\rho n)^2 + (\rho k)^2}{(1+\rho n)^2 + (\rho k)^2}\right]\left[\cosh\left(\frac{4\pi hk}{\lambda}\right) - \cos\left(\frac{4\pi hn}{\lambda}\right)\right]}{e^{\frac{4\pi kh}{\lambda}} + \left[\frac{(1-\rho n)^2 + (\rho k)^2}{(1+\rho n)^2 + (\rho k)^2}\right]^2\left[e^{-\frac{4\pi hk}{\lambda}}\right]^{-2}\left[\frac{(1-\rho n)^2 + (\rho k)^2}{(1+\rho n)^2 + (\rho k)^2}\right]\cos\left(\frac{4\pi n}{\lambda} - 4r^2\right)}$$

$$\frac{T_2}{I_2} = \frac{16\left[\frac{(\rho n)^2 + (\rho k)^2}{[(1+\rho n)^2 + (\rho k)^2]^2}\right]}{e^{\frac{4\pi kh}{\lambda}} + \left[\frac{(1-\rho n)^2 + (\rho k)^2}{(1+\rho n)^2 + (\rho k)^2}\right]\left[e^{-\frac{4\pi hk}{\lambda}}\right]^{-2}\left[\frac{(1-\rho n)^2 + (\rho k)^2}{(1+\rho n)^2 + (\rho k)^2}\right]\cos\left(\frac{4\pi n}{\lambda} - 4r^2\right)}$$

$$\frac{R_1}{I_1} = \frac{\left[\frac{2(\rho n - N^2 + K^2)^2 + (\rho k - 2NK)^2}{(\rho n + N^2 - K^2)^2 + (\rho k + 2NK)^2}\right]\left[\cosh\left(\frac{4\pi kh}{\lambda}\right) - \cos\left(\frac{4\pi hn}{\lambda}\right)\right]}{e^{\frac{4\pi kh}{\lambda}} + \left[\frac{(\rho n - N^2 + K^2)^2 + (\rho k - 2NK)^2}{(\rho n + N^2 - K^2)^2 + (\rho k + 2NK)^2}\right]^2\left[e^{-\frac{4\pi kh}{\lambda}}\right]^{+2}\left[\frac{(\rho n - N^2 + K^2)^2 + (\rho k - 2NK)^2}{(\rho n + N^2 - K^2)^2 + (\rho k + 2NK)^2}\right]\left[\cos\left(\frac{4\pi n}{\lambda} - 4r^2\right)\right]}$$

-continued $$\frac{T_1}{I_1} = \frac{16\left[\frac{[(\rho n)^2 + (\rho k)^2][(N^2 - K^2)^2 + (2NK)^2]}{(\rho n + N^2 - K^2)^2 + (\rho k + 2NK)^2]^2}\right]}{e^{\frac{4\pi hk}{\lambda}} + \left[\frac{(\rho n - N^2 + K^2)^2 + (\rho k - 2NK)^2}{(\rho n + N^2 - K^2)^2 + (\rho k + 2NK)^2}\right]^2 \left[e^{-\frac{4\pi hk}{\lambda}}\right] + 2\left[\frac{(\rho n - N^2 + K^2)^2 + (\rho k - 2NK)^2}{(\rho n + N^2 - K^2)^2 + (\rho k + 2NK)^2}\right]\left[\cos\left(\frac{4\pi n}{\lambda} - \phi r^2\right)\right]}$$

The indices of equations (5) may be similarly set forth in more rigorous form as:

$$n = \alpha n_w + \beta n_p + 1 - \alpha - \beta$$

$$K = \alpha K_w + \beta K_p \qquad (20)$$

where
- $\alpha$ is the thickness fraction of water
- $\beta$ is the thickness fraction of pulp, and
- $(1-[\alpha+\beta])$ is the thickness fraction of air.

Solution of these equations yields values of moisture, caliper, and basis weight. The theoretical basis of these equations is set forth in the appendix.

As shown in FIG. 2, oscillators 12 and 14 include temperature sensors 13 and 15, respectively. Temperature sensors 13 and 15 generate signals proportional to the temperature of their respective Gunn diode oscillators and are connected to signal processor 32 to provide signals indicative of incident radiation supplied to web 18. Temperature sensors 13 and 15 thus constitute incident signal generating means for generating a separate incident signal for each of the beams supplied by oscillators 12 and 14, the incident signals being proportional to energy incident upon web 18. Other means of supplying an incident signal could of course be employed. Signal processor 32 then produces a signal indicative of the transmittance-to-incident and reflectance-to-incident ratios.

Figure 8:
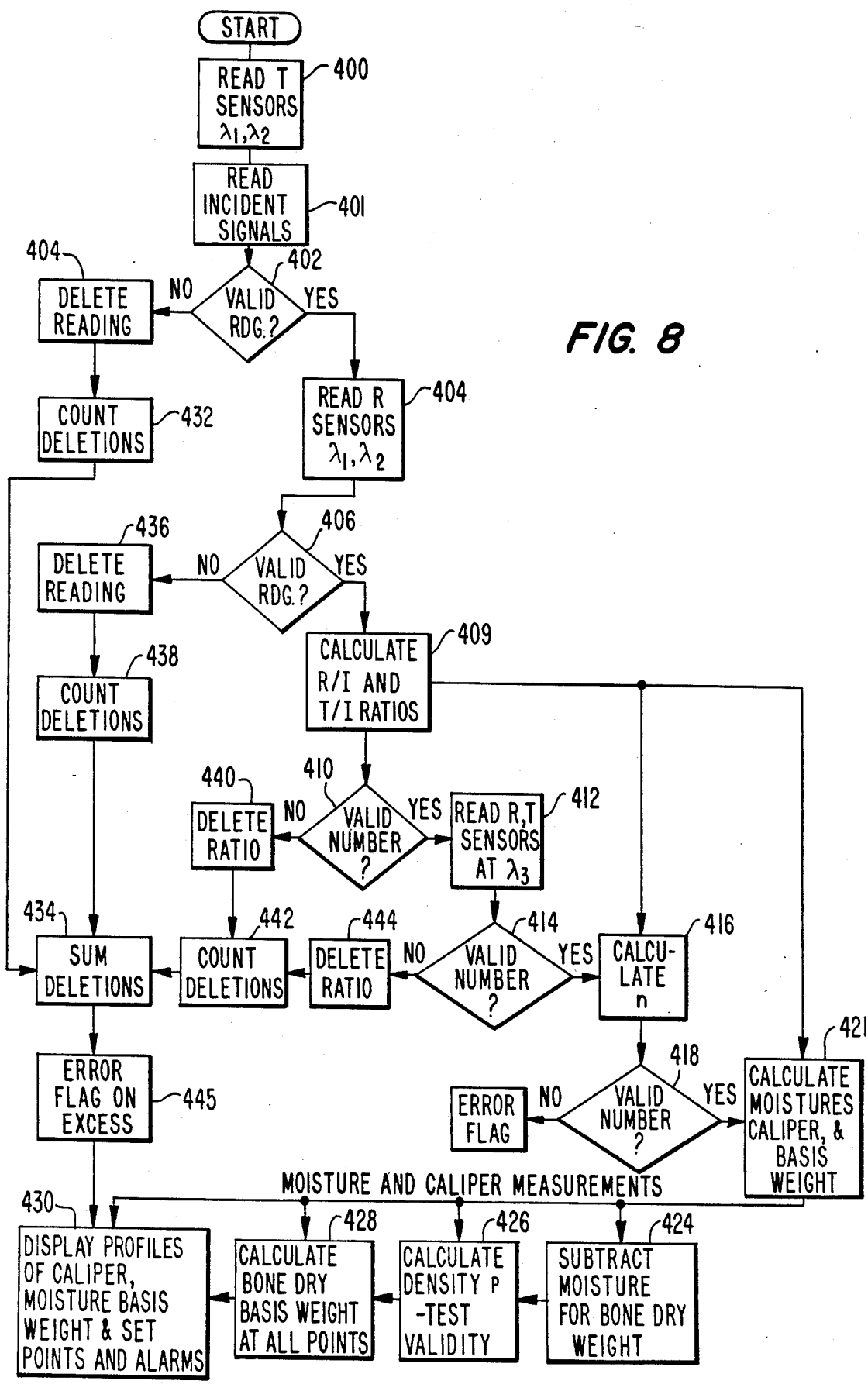
FIG. 8 is a flow chart similar to FIG. 7 for an alternative embodiment in which basis weight is calculated from incident, reflectance, and transmittance signals.

The processing of values by computer 34 in the alternative embodiment is set forth in FIG. 8. This flow chart is similar to FIG. 7; thus only the differences will be discussed.

After transmittance sensors are read in block 400, a signal indicative of incident power to web 18 is read at block 401. Processing continues as in FIG. 7 until block 409, where reflectance-to-incident (R/I) and transmittance-to-incident (T/I) ratios are calculated. Flow then procedes to block 421 where moisture, caliper, and basis weight are calculated. In all other respects, logic flow occurs as previously set forth with respect to FIG. 7.

It will be recognized by one skilled in the art that other changes and modifications in the described embodiment can be performed without departing from the scope of the invention, which is intended to be limited only by the scope of the appended claim.

APPENDIX

Let A be the amplitude of the incident wave A of FIG. 1 which is a complex quantity. For each member A1, A2 ... AN, B1, B2 ... BN of either the reflected or the transmitted set of waves, the variable part of the phase of the wave function differs from that of the preceding member by an amount which corresponds to a double traversal of the medium. This phase difference is $$\delta = \frac{4\pi Nh}{\lambda} \cos\theta'$$

where h is the thickness of the medium, $\lambda$ is the wavelength in the air and $\tilde{N}$ is the complex index of refraction of the medium.

If all the reflected waves are superposed, the amplitude of the reflected wave is given by the expression $$A^{(r)} = r\left[\frac{e^{j2\alpha\tilde{n}} - 1}{e^{j2\alpha\tilde{n}} - r^2}\right]A^{(i)}$$

where
A:

$$\alpha = \frac{2\pi h}{\lambda}$$

N: is the real part of the index of refraction
K: is the imaginary part of the index of refraction (absorption) also $\tilde{n} = \tilde{N}\cos\theta'$. The relation between $\tilde{n}$ and $\tilde{N}$ are as follows:

$$\tilde{n} = n - jk = \tilde{N}\cos\theta' = [N - jK]\cos\theta'$$

$$\tilde{N}\sin\theta' = \sin\theta; \sin\theta' = \frac{\sin\theta}{\tilde{N}}; \sin^2\theta' = \frac{\sin^2\theta}{\tilde{N}^2}$$

$$\cos^2\theta' = 1 - \sin^2\theta' = \frac{\tilde{N}^2 - \sin^2\theta}{\tilde{N}^2};$$

$$\tilde{N}^2\cos^2\theta' = \tilde{N}^2 - \sin^2\theta$$

$$\tilde{N}\cos\theta' = n - jk; (n - jk)^2 = (N - jK)^2 - \sin^2\theta$$

$$n^2 - k^2 - 2jnk = N^2 - K^2 - 2jNK - \sin^2\theta$$

$$n = N\cos\theta'$$
$$k = K\cos\theta'$$

Equating the real and imaginary parts yields.

$$n^2 - k^2 = N^2 - K^2 - \sin^2\Theta$$

$$nk = NK; N^2K^2 = n^2k^2; k^2 = \frac{N^2K^2}{n^2}$$

$$n^2 - \frac{N^2K^2}{n^2} = N^2 - K^2 - \sin^2\Theta$$

$$n^4 - n^2[N^2 - K^2 - \sin^2\Theta] - N^2K^2 = 0$$

Solution of the immediately preceding equation yields:

$$n^2 = \frac{N^2 - K^2 - \sin^2\Theta + \sqrt{(N^2 - K^2 - \sin^2\Theta)^2 + 4N^2K^2}}{2}$$

$$n = \left[\frac{N^2 - K^2 - \sin^2\Theta + \sqrt{(N^2 - K^2 - \sin^2\Theta)^2 + 4N^2K^2}}{2}\right]^{\frac{1}{2}}$$

In a similar manner:

$$k = \left[\frac{-[N^2 - K^2 - \sin^2\Theta] + \sqrt{(N^2 - K^2 - \sin^2\Theta)^2 + 4N^2K^2}}{2}\right]^{\frac{1}{2}}$$

$$\frac{A(r)}{A(i)} = r\left[\frac{e^{j2\alpha(n-jk)} - 1}{e^{j2\alpha(n-jk)} - r^2}\right] = r\left[\frac{e^{2\alpha k}e^{j2\alpha n} - 1}{e^{2\alpha k}e^{j2\alpha n} - r^2}\right]$$

The power R of the reflected wave is given by $$R = A^{(r)} A^{(r)*}$$

$$I = A^{(i)} A^{(i)*}$$

$$\frac{R}{I} = \left[r\left[\frac{e^{2\alpha k}e^{j2\alpha n} - 1}{e^{2\alpha k}e^{j2\alpha n} - r^2}\right]\right]\left[r\left[\frac{e^{2\alpha k}e^{ja2n} - 1}{e^{2\alpha k}e^{ja2n} - r^2}\right]\right]*$$

$$\frac{R}{I} = r\left[\frac{e^{2\alpha k}e^{j2\alpha n} - 1}{e^{2\alpha k}e^{j2\alpha n} - r^2}\right]r*\left[\frac{e^{2\alpha k}e^{-j2\alpha n} - 1}{e^{2\alpha k}e^{-j2\alpha n} - r^{2*}}\right]$$

$$\frac{R}{I} = |r|^2 \frac{[e^{4\alpha k} - e^{2\alpha k}e^{j2\alpha n} - e^{2\alpha k}e^{-j2\alpha n} + 1]}{[e^{4\alpha k} - r^{2*}e^{2\alpha k}e^{j2\alpha n} - r^2 e^{2\alpha k}e^{j2\alpha n} + |r|^4]}$$

$$\frac{R}{I} = |r|^2 e^{2\alpha k}\left[\frac{e^{2\alpha k} + e^{-2\alpha k} - (e^{j2\alpha n} + e^{j2\alpha n})}{e^{2\alpha k}e^{2\alpha k} + |r|^4 e^{-2\alpha k} - (r^{2*}e^{j2\alpha n} + r^2 e^{-j2\alpha n})}\right]$$

$$\frac{R}{I} = 2|r|^2 \frac{\left[\frac{(e^{2\alpha k} + e^{-2\alpha k})}{2} - \frac{(e^{j2\alpha n} + e^{-j2\alpha n})}{2}\right]}{[e^{2\alpha} + |r|^4 e^{-2\alpha k} - r^{2*}e^{j2\alpha n} + r^2 e^{-j2\alpha n}]}$$

$$\frac{R}{I} = 2|r|^2 \left[\frac{\cosh(2\alpha k) - \cos(2\alpha n)}{e^{2\alpha k} + |r|^4 e^{-2\alpha k} - 2|r|^2 \cos(2\alpha n - \sphericalangle r^2)}\right]$$

In a similar way if all the transmitted waves are superposed, the amplitude of the transmitted wave is given by the expression:

$$A^{(t)} = \left[\frac{(1 - r^2) e^{\alpha \bar{n}}}{(e^{2\alpha n} - r^2)}\right] A^{(i)}$$

$$\frac{A^{(t)}}{A^{(i)}} = \left[\frac{(1 - r^2) e^{\alpha} e^{j\alpha n}}{(e^{2\alpha} e^{j2\alpha n} - r^2)}\right]$$

The power T of the transmitted wave is given by:

$$T = A^{(t)} A^{(t)*}$$

$$\frac{T}{I} = \left[\frac{(1 - r^2) e^{\alpha k} e^{j\alpha n}}{e^{2\alpha k} e^{j2\alpha n} - r^2}\right]\left[\frac{(1 - r^2) e^{\alpha k} e^{j\alpha n}}{e^{2\alpha k} e^{j2\alpha n} - r^2}\right]*$$

$$\frac{T}{I} = \frac{|1 - r^2|^2 e^{2\alpha k}}{e^{2\alpha k}[e^{2\alpha k} + |r|^{44} e^{-2\alpha k} - 2|r|^2 \cos(2\alpha n - \sphericalangle r^2)]}$$

$$\frac{T}{I} = \frac{|1 - r^2|^2}{e^{2\alpha k} + |r|^4 e^{-2\alpha k} - 2|r|^2 \cos(2\alpha n - \sphericalangle r^2)}$$

In the case when the electric vector is perpendicular to the plane of incidence ("TE wave" ... case of the 47 GHz):

$$r = -r_{10} = \frac{\cos\Theta - \bar{N}\cos\Theta'}{\cos\Theta + \bar{N}\cos\Theta'} = \frac{\cos\Theta - (n - jk)}{\cos\Theta + n - jk}$$

$$r = \frac{1 - \frac{n}{\cos\Theta} + j\frac{k}{\cos\Theta}}{1 + \frac{n}{\cos\Theta} + \frac{jk}{\cos\Theta}}$$

$$\rho = \frac{1}{\cos\Theta}$$

$$r = \frac{(1 - \rho n) + j\rho k}{(1 + \rho n) - j\rho k} \;;\; |r|^2 = \frac{(1 - \rho n)^2 + (\rho k)^2}{(1 + \rho n)^2 + (\rho k)^2}$$

$$|r|^4 = \left[\frac{(1 - \rho n)^2 + (\rho k)^2}{(1 + \rho n)^2 + (\rho k)^2}\right]^2$$

The phase of r² is:

$$\sphericalangle r^2 = 2\sphericalangle r = 2\left[\tan^{-1}\left(\frac{\rho k}{1 - \rho n}\right) + \tan^{-1}\left(\frac{\rho k}{1 + \rho n}\right)\right]$$

$$|1 - r^2|^2 = 16\left[\frac{(\rho n)^2 + (\rho k)^2}{[(1 + \rho n)^2 + (\rho k)^2]^2}\right]$$

The final form of the ratio of the power of the reflected wave to the incident wave is:

$$\frac{R}{I} = \frac{2\left[\frac{(1 - \rho n)^2 + (k)^2}{(1 + \rho n)^2 + (\rho k)^2}\right]\left[\cosh\left(\frac{4\pi hk}{\lambda}\right) - \cos\left(\frac{4\pi hn}{\lambda}\right)\right]}{e^{\frac{4\pi kh}{\lambda}} + \left[\frac{(1 - \rho n)^2 + (\rho k)^2}{(1 + \rho n)^2 + (\rho k)^2}\right]^2 \left[e^{\frac{-4\pi hk}{\lambda}}\right] - 2\left[\frac{(1 - n)^2 + (k)^2}{(1 + n)^2 + (k)^2}\right]\left[\cos\left(\frac{4\pi n}{\lambda} - \sphericalangle r^2\right)\right]}$$

Similarly the power ratio of the transmitted wave to the incident wave is:

$$\frac{T}{I} = \frac{16\left[\frac{[(\rho n)^2 + (\rho k)^2]}{[(1+\rho n)^2 + (\rho k)^2]^2}\right]}{\left[e^{\frac{4\pi kh}{\lambda}} + \left[\frac{(1-\rho n)^2 + (\rho k)^2}{(1+\rho n)^2 + (\rho k)^2}\right]^2\right]\left[e^{\frac{-4\pi hk}{\lambda}}\right]^{-2}\left[\frac{(1-\rho n)^2 + (\rho k)^2}{(1+\rho n)^2 + (\rho k)^2}\right]\left[\cos\left(\frac{4\pi n}{\lambda} - r^2\right)\right]}$$

The power ratio of the reflected wave and the transmitted wave can also be calculated as:

$$\frac{R}{T} = \frac{[[(\rho n^2 - (\rho k)^2 - 1]^2 + 4(\rho n)^2(\rho k)^2]\left[\cosh\left(\frac{4\pi hk}{\lambda}\right) - \cos\left(\frac{4\pi hn}{\lambda}\right)\right]}{8[(\rho n)^2 + (\rho k)^2]}$$

For a TM wave where the electric vector is parallel to the plane of incidence:

$$r = -r_{10} = -\left[\frac{\tilde{N}\cos\Theta - \cos\Theta'}{\tilde{N}\cos\Theta + \cos\Theta'}\right] =$$

$$\left[\frac{\tilde{N}\cos\Theta' - N^2\cos\Theta}{\tilde{N}\cos\Theta' + N^2\cos\Theta}\right]$$

$$r = \frac{n - jk - (N - jK)^2\cos\Theta}{n - jk + (N - jK)^2\cos\Theta} =$$

$$\frac{\rho n - j\rho k - N^2 + K^2 + 2jNK}{\rho n - j\rho k + N^2 + K^2 - 2jNK}$$

$$r = \frac{(\rho n - N^2 + K^2) - j(\rho k - 2NK)}{(\rho n + N^2 + K^2) - j(\rho k + 2NK)}$$

$$|r|^2 = \frac{(\rho n - N^2 + K^2)^2 + (\rho k - 2NK)^2}{(\rho n + N^2 + K^2)^2 + (\rho k + 2NK)^2}$$

$$|r^2|^2 = |r|^4$$

$$\mathcal{Q}r^2 = 2\mathcal{Q}r =$$

$$2\left[\tan^{-1}\left[\frac{k + 2NK}{n + N^2 - K^2}\right] - \tan^{-1}\left[\frac{k - 2NK}{n - N^2 + K^2}\right]\right]$$

$$|1 - r^2|^2 = \frac{16(\rho n)^2 + (\rho k)^2(N^2 + K^2)^2 + (2NK)^2}{[(\rho n + N^2 - K^2)^2 + (\rho k + 2NK)^2]^2}$$

In a preferred embodiment of the invention, the medium is paper. The paper is composed of a mixture of water, air, pulp and filler. The optical path can be modeled as the sum of the optical paths through the paper, i.e., $$L = \sum_{j=1}^{3} H_j \tilde{N}_j = H\tilde{N}$$

where L is the optical path, $H_j$ the thickness of $j^{th}$ material and $\tilde{N}_j$ is the complex index of refraction of the $j^{th}$ material. So the total thickness H is $$H = \sum_{1}^{3} H_j$$

Let $\tilde{N}$ be the index of refraction of the paper $$\tilde{N}H = H_w\tilde{N}_w + H_p\tilde{N}_p + H_a\tilde{N}_a$$

where
w means water
p means pulp
a means air
but $$\tilde{N} = N - jk;\ \tilde{N}_w = N_w - jkw;\ \tilde{N}_p = N_p - jkp;\ \tilde{N}_a = N_a - jka$$

$$H(N - jk) = H_w(N_w - jkw) + H_p(N_p - jkp) + H_a(N_a - jka)$$

$$HN - jHK = H_wN_w + H_pN_p + H_aN_a - j[H_wK_w + H_pK_p + H_aK_a]$$

The real parts are equal so:

$$NH = N_wH_w + H_pN_p + N_aH_a$$

and $n = \frac{H_w}{H}N_w + \frac{H_p}{H}N_p + \frac{H_a}{H}N_a$

The index of the air is known $N_a=1$ and $K_a=0$. If it is assumed that $$\alpha = \frac{H_w}{H}\ \text{and}\ 1 - (\alpha + \beta) = \frac{H_a}{H}$$

then $N = \alpha N_w + \beta N + (1 - (\alpha + \beta))$ where
α is the thickness fraction of water
β is the thickness fraction of pulp
The same form holds for the imaginary part of the index $$K = \alpha K_w + \beta I_p + [1 - (\alpha + \beta)]K_a$$

but
$K_a = 0$
$K = \alpha K_w + \beta K_p$

The indices of water and pulp are experimentally obtained values so nw, np, Kw, Kp are known at both frequencies 94 GHz and 47 GHz. Knowing the equation for R/I and I/I allows replacement of the indices of the medium by the indices of the paper which are $$N = \alpha N_w + \beta N_p + 1 - \alpha - \beta$$

$$K = \alpha K_w + \beta K_p$$

In equations of R/I and I/I there are three unknowns which are α, B, H.

Operating on two different frequencies 94 GHz and 47 GHz four measurements $R_1/I_1$, $R_2/I_2$, $T_1/I_1$, $T_2/I_2$ can be made.

Solving these four equations for the three unknown yields:

α the fraction (thickness) of water
β the thickness fraction of pulp
H the caliper of the paper H
The dry basis weight of the paper is $$B_d = \rho_p H_p + \rho_a H_a$$

$$B_d = \rho_p \beta H + \rho_a(1-(\alpha+\beta))H$$

where $\rho_p$ is the density of the pulp and $\rho_a$ the density of air (very small).

Also, the basis weight of water is $$B_w = \rho_w \alpha H$$

where $\rho_w$ is density of water

Having calculated the basis weight of dry material and of moisture, the percent weight of moisture can be calculated as:

$$M = \frac{B_w}{B_w + B_d} \times 100 = \text{Moisture \%}$$

What is claimed is:

1. Apparatus for sensing the characteristics of sheet material, comprising:
   radiating means for generating a plurality of beams of coherent electromagnetic radiation, each of said beams having a different frequency, and for directing said beams against said material at an area of incidence;
   first signal generating means for generating separate reflectance and transmittance signals for each of said beams, said signals being proportional to the intensity of each of said beams reflected from and transmitted through said material, respectively; and
   processing means for producing moisture and thickness signals calculated from said plurality of reflectance and transmittance signals.

2. Apparatus as recited in claim 1 wherein said beams are stationary.

3. Apparatus as recited in claim 2 comprising a plurality of said radiating means each directing its associated plurality of beams against a separate area of incidence, said separate areas of incidence being spatially distributed across said material,
   wherein said processing means produces separate moisture and thickness signals for each of said radiating means, and
   whereby spatial profiles of moisture and thickness characteristics are produced for said material.

4. Apparatus as recited in claim 3 wherein said radiating means comprises means for generating microwave radiation.

5. Apparatus as recited in claim 4 wherein said means for generating microwave radiation generates radiation having a wavelength greater than four times the thickness of said material.

6. Apparatus as recited in claim 4 comprising second generating means for generating a reference signal proportional to basis weight at a reference position and wherein said processing means generates a spatial profile of basis weight of said material calculated from said reference signal and said moisture and thickness signals.

7. Apparatus as recited in claim 6 wherein said radiating means comprises transmitting antennas and reflectance receiving antennas in a stationary position on one side of the plane of a moving web of said material and transmittance receiving antennas in a stationary position on the opposite side of said plane of a moving web of said material.

8. Apparatus as recited in claim 6 wherein said second generating means comprises means for generating a beam of particles.

9. Apparatus as recited in claim 8 wherein said second generating means comprises means for generating a beam of electrons.

10. Apparatus as recited in claim 9 wherein said second generating means comprises a radioactive source of beta radiation.

11. Apparatus as recited in claim 9 wherein said second generating means comprises an electron gun.

12. Apparatus as recited in claim 1 wherein said reflectance and transmittance signals are respectively proportional to the intensity of each of said beams reflected from and transmitted through said material.

13. Apparatus as recited in claim 1 wherein said processing means comprises means for solving simultaneous equations which include functions of moisture content, thickness, and complex index of refraction of said material.

14. Apparatus as recited in claim 4 wherein said processing means comprises means for solving a plurality of simultaneous equations including functions of moisture content, thickness, and complex index of refraction of said material at the frequencies of said beams.

15. Apparatus for sensing the characteristics of sheet material, comprising:
   a plurality of radiating means for generating coherent microwave electromagnetic radiation, each of said radiating means generating a plurality of beams having a different frequency, and, each of said radiating means directing its associated plurality of beams against a separate area of incidence, said separate areas of incidence being spatially distributed across said material;
   first signal generating means for generating separate reflectance and transmittance signals for each of said beams, said signals being proportional to the intensity of each of said beams reflected from and transmitted through said material, respectively;
   second generating means for generating a reference signal proportional to basis weight at a reference position; and
   processing means for producing separate moisture and thickness signals for each of said radiating means calculated from said plurality of reflectance and transmittance signals and from said reference signal; said processing means generating a spatial profile of moisture and thickness across said material.

16. A method for simultaneously sensing a plurality of characteristics of sheet material, comprising the steps of:
   generating a plurality of beams of coherent electromagnetic radiation, each of said beams having a different frequency;
   directing said plurality of beams against the material at a area of incidence;

generating separate reflectance and transmittance signals for each of said beams proportional to the amount of each of said beams reflected from and transmitted through said material, respectively; and calculating moisture content and thickness from said reflectance and transmittance signals.

17. A method for simultaneously sensing a plurality of characteristics of sheet material, comprising the steps of:

generating a plurality of groups of beams of coherent electromagnetic radiation, each beam in a group having a different frequency from the other beams of the group;

directing each group of beams against the material at a different area of incidence;

generating separate reflectance and transmittance signals for the beams proportional to the intensity of each of the beams reflected from and transmitted through the material, respectively; and calculating values representative of the moisture content and thickness of the said material from said reflectance and transmittance signals at each of said areas of incidence to generate a moisture content and thickness spatial profile of the material.

18. A method as recited in claim 17 comprising the additional steps of:

generating a reference signal proportional to basis weight of said material at one of the areas of incidence; and calculating a plurality of basis weight values from said reference signal and said values representative of moisture content and thickness to generate a basis weight spatial profile of said material.

19. A method as recited in claim 18 wherein said step of generating a reference signal comprises the steps of directing a beam of electrons through said material and measuring the amount of said electron beam energy transmitted through said material.

20. A method as recited in claim 18 comprising the step of generating a plurality of dry basis weight signals from said basis weight values and said moisture content values to generate a spatial profile of dry basis weight for said material.

21. A method as recited in claim 17 wherein the step of generating a plurality of groups of beams of electromagnetic radiation comprises the step of generating a plurality of microwave signals.

22. Apparatus for analyzing sheet material, comprising:

a reflectance unit comprising:
a first radiation source for generating a first beam of coherent electromagnetic radiation,
a second radiation source for generating a second beam of coherent electromagnetic radiation having a frequency different from said first beam,
first focusing means for collimating said first and second beams and for directing said first and second beams against the material to be analyzed,
second focusing means for receiving said first and second beams reflected from the material to be analyzed; and
first and second reflectance detector means for generating first and second reflectance signals responsive to the intensity of said reflected first and second beams, respectively;

a transmittance unit adapted for mounting on the side of the material to be analyzed opposite from said reflectance unit, said transmittance unit comprising first and second transmittance detector means for generating first and second transmittance signals respectively responsive to the intensity of said first and second beams transmitted through the material to be analyzed;

means for generating first and second incident signals indicative of the intensity of said first and second beams applied to said material; and means for processing said incident, reflectance, and transmittance signals to produce signals representative of characteristics of the material being analyzed.

23. Apparatus for analyzing sheet material, comprising:

a reflectance unit comprising:
a first radiation source for generating a first beam of coherent electromagnetic radiation,
a second radiation source for generating a second beam of coherent electromagnetic radiation having a frequency different from said first beam,
first focusing means for collimating said first and second beams and for directing said first and second beams against the material to be analyzed,
second focusing means for receiving said first and second beams reflected from the material to be analyzed; and
first and second reflectance detector means for generating first and second reflectance signals responsive to the intensity of said reflected first and second beams, respectively;

a transmittance unit adapted for mounting on the side of the material to be analyzed opposite from said reflectance unit, said transmittance unit comprising first and second transmittance detector means for generating first and second transmittance signals respectively responsive to the intensity of said first and second beams transmitted through the material to be analyzed; and means for processing said reflectance and transmittance signals to produce signals representative of characteristics of the material being analyzed.

24. Apparatus as recited in claim 2 comprising a beam combiner downstream from said radiation sources directing said first and second beams of electromagnetic radiation along a common path.

25. Apparatus as recited in claim 24 comprising:
a reflectance beam splitter downstream from said second focusing means directing said reflected first and second beams into said first and second reflectance detector means, respectively; and
a transmittance beam splitter downstream from said transmittance focusing means directing said transmitted first and second beams into said first and second transmittance detector means, respectively.

26. Apparatus as recited in claim 25 wherein said reflectance unit comprises reflectance means for reflecting at least one of said first and second beams from its respective radiation source to said beam combiner.

27. Apparatus as recited in claim 26 wherein said reflectance means reflects said first and second beams from their respective radiation sources to said beam combiner.

28. Apparatus as recited in claim 27 wherein said reflectance means comprise an off-axis paraboloid mirror.

29. Apparatus as recited in claim 25 wherein said first and second reflectance focusing means each comprise a lens of dielectric material, said first reflectance focusing means lens having a different output beam waist size than the input beam waist size of said second reflectance focusing means lens.

30. Apparatus as recited in claim 29 wherein said first reflectance focusing means lens has a larger output beam waist size than the input beam waist size of said second reflectance focusing means lens.

31. Apparatus as recited in claim 25 comprising a transmittance mounting board and a pair of said transmittance units mounted on opposite sides of said transmittance mounting board to form a transmittance module.

32. Apparatus as recited in claim 31 comprising a reflectance mounting board and a pair of said reflectance units mounted on opposite sides of said reflectance mounting board to form a reflectance module.

33. Apparatus as recited in claim 32 comprising:
a plurality of said transmittance modules,
a plurality of said reflectance modules equal in number to the number of said transmittance modules,
means for connecting each of said transmittance and reflectance detectors to said processing means,
a transmittance frame supporting said transmittance modules juxtaposed in a horizontal plane,
a reflectance frame supporting said reflectance modules juxtaposed parallel to said horizontal plane, and
means for supporting said reflectance and transmittance frames in a manner so as to define an elongated opening therebetween parallel to said horizontal plane and adapted to receive a moving web of material to be analyzed, said supporting means supporting each of said reflectance modules in vertical alignment with a corresponding one of said transmittance modules.

34. Apparatus as recited in claim 33 wherein said transmittance modules are positioned above said elongated opening and said reflectance modules are positioned below said elongated opening.

35. Apparatus as recited in claim 32 wherein each of said reflectance units comprises a first modulator producing modulation of a first modulation type on said first beam and a second modulator producing a second modulation type on second beam.

36. Apparatus as recited in claim 35 wherein said first modulators of adjacent reflectance units produce modulation of different frequencies.

37. Apparatus as recited in claim 35 wherein said reflectance frame comprises a plurality of control devices, each of said control devices being removably connected to one of said reflectance units, and said modulators are responsive to said control devices to establish the modulation frequency of each of said modulators.

38. Apparatus for sensing the characteristics of sheet material, comprising:
radiating means for generating a plurality of beams of coherent electromagnetic radiation, each of said beams having a different frequency, and for directing said beams against said material at an area of incidence;
first signal generating means for generating separate reflectance and transmittance signals for each of said beams, said signals being proportional to the intensity of each of said beams reflected from and transmitted through said material, respectively;
incident signal generating means for generating a separate incident signal for each of said beams, said incident signal being proportional to energy incident upon said material; and
processing means for producing moisture, thickness, and basis weight signals calculated from said plurality of reflectance, transmittance, and incident signals.

39. Apparatus as recited in claim 38 wherein said beams are stationary.

40. Apparatus as recited in claim 39 comprising a plurality of said radiating means each directing its associated plurality of beams against a separate area of incidence, said separate areas of incidence being spatially distributed across said material,
wherein said processing means produces separate moisture, thickness, and basis weight signals for each of said radiating means, and
whereby spatial profiles of moisture, thickness, and basis weight characteristics are produced for said material.

41. Apparatus as recited in claim 40 wherein said radiating means comprises means for generating microwave radiation.

42. Apparatus as recited in claim 41 wherein said means for generating microwave radiation generates radiation having a wavelength greater than four times the thickness of said material.

43. Apparatus as recited in claim 38 wherein said reflectance and transmittance signals are respectively proportional to the intensity of each of said beams reflected from and transmitted through said material.

44. Apparatus as recited in claim 38 wherein said processing means comprises means for solving simultaneous equations which include functions of moisture content, thickness, and complex index of refraction of said material.

45. Apparatus as recited in claim 41 wherein said processing means comprises means for solving a plurality of simultaneous equations including functions of moisture content, thickness, and complex index of refraction of said material at the frequencies of said beams.

46. Apparatus as recited in claim 38 wherein said beams have different polarization.

47. Apparatus as recited in claim 46 wherein said radiating means generates a pair of orthogonally polarized beams.

48. A method for simultaneously sensing a plurality of characteristics of sheet material, comprising the steps of:
generating a plurality of beams of coherent electromagnetic radiation, each of said beams having a different frequency;
directing said plurality of beams against the material at a area of incidence;
generating separate incident, reflectance, and transmittance signals for each of said beams proportional to the amount of each of said beams applied to, reflected from, and transmitted through said material, respectively; and calculating moisture content, thickness, and basis weight from said incident, reflectance, and transmittance signals.

49. A method for simultaneously sensing a plurality of characteristics of sheet material, comprising the steps of:
generating a plurality of groups of beams of coherent electromagnetic radiation, each beam in a group having a different frequency from the other beams of the group;
directing each group of beams against the material at a different area of incidence;
generating separate incident, reflectance, and transmittance signals for the beams proportional to the intensity of each of the beams applied to, reflected from, and transmitted through the material, respectively; and
calculating values representative of the moisture content, thickness, and basis weight of the said material from said incident, reflectance, and transmittance signals at each of said areas of incidence to generate a moisture content, thickness, and basis weight spatial profile of the material.

50. A method as recited in claim 49 wherein the step of generating a plurality of groups of beams of electromagnetic radiation comprises the step of generating a plurality of microwave signals.

* * * * *

UNITED STATES PATENT AND TRADEMARK OFFICE
CERTIFICATE OF CORRECTION

PATENT NO. : 4,789,820
DATED : DECEMBER 6, 1988
INVENTOR(S) : KHAZEN, PARRENT, REILLY & ZEIDERS

It is certified that error appears in the above-identified patent and that said Letters Patent is hereby corrected as shown below:

Column 1, Line 42

"desireable" should read --desirable--

Patent: Column 4, Line 7

"thorugh" should read --through--

Column 7, Line 14

"corporation" should read --Corporation--

Column 9, Line 52

"analyed" should read --analyzed--

Column 11, Line 24

"positon" should read --position--.

UNITED STATES PATENT AND TRADEMARK OFFICE
CERTIFICATE OF CORRECTION

PATENT NO. : 4,789,820
DATED : DECEMBER 6, 1988
INVENTOR(S) : KHAZEN, PARRENT, REILLY & ZEIDERS

It is certified that error appears in the above-identified patent and that said Letters Patent is hereby corrected as shown below:

Column 4, Line 54

"Sin$^2$" should read --sin$^2$--

Column 12, Line 39

"18." should read --18'.--

Column 18, Line 51

"K=aKw+BIp..." should read --K=aKw+Bkp...--

Column 19, Line 4

"unknown" should read --unknowns--.

Signed and Sealed this

Twenty-second Day of August, 1989

Attest:

DONALD J. QUIGG

*Attesting Officer*     Commissioner of Patents and Trademarks